United States Patent
Roy et al.

(10) Patent No.: US 7,965,810 B2
(45) Date of Patent: Jun. 21, 2011

(54) DEVICE AND METHOD FOR IDENTIFYING OCCLUSIONS

(75) Inventors: Arunabha S. Roy, Banglore (IN); James Vradenburg Miller, Clifton Park, NY (US); Paulo Ricardo (dos Santos) Mendonca, Clifton Park, NY (US); Rahul Bhotika, Albany, NY (US); Ajay Gopinath, Karnataka (IN); Robert Franklin Senzig, Germantown, WI (US); Wesley David Turner, Rexford, NY (US); Srikanth Suryanarayanan, Karnataka (IN)

(73) Assignee: General Electric Company, Schenectady, NY (US)

( * ) Notice: Subject to any disclaimer, the term of this patent is extended or adjusted under 35 U.S.C. 154(b) by 1017 days.

(21) Appl. No.: 11/768,623

(22) Filed: Jun. 26, 2007

(65) Prior Publication Data

US 2009/0003511 A1 Jan. 1, 2009

(51) Int. Cl.
*A61B 6/00* (2006.01)
*G06K 9/00* (2006.01)
(52) U.S. Cl. ............................... 378/4; 382/131
(58) Field of Classification Search .................. 382/128, 382/129, 130, 131, 132, 133, 134, 164, 171, 382/173; 378/98.12, 41, 4–21, 101, 140, 378/901; 600/300, 407, 410, 423, 433, 443; 128/915, 920, 922, 898
See application file for complete search history.

(56) References Cited

U.S. PATENT DOCUMENTS

| | | | |
|---|---|---|---|
| 6,251,072 B1* | 6/2001 | Ladak et al. | 600/443 |
| 7,468,040 B2* | 12/2008 | Hartley et al. | 600/529 |
| 7,738,626 B2* | 6/2010 | Weese et al. | 378/41 |
| 2002/0009215 A1* | 1/2002 | Armato et al. | 382/131 |
| 2005/0226360 A1 | 10/2005 | Kaucic, Jr. et al. | |
| 2005/0240094 A1 | 10/2005 | Pichon et al. | |
| 2006/0023925 A1 | 2/2006 | Kiraly et al. | |
| 2006/0025674 A1 | 2/2006 | Kiraly et al. | |
| 2006/0079743 A1* | 4/2006 | Ferrant et al. | 600/407 |
| 2007/0092864 A1* | 4/2007 | Reinhardt et al. | 435/4 |

OTHER PUBLICATIONS

Yoshitaka Masutani, et al., "Computerized Detection of Pulmonary Embolism in Spiral CT Angiography Based on Volumetric Image Analysis", IEEE Transactions on Medical Imaging, vol. 21, No. 12, Dec. 2002.

C. Zhou, et al., "Preliminary Investigation of Computer-aided Detection of Pulmonary Embolism in Three dimensional Computed Tomography Pulmonary Angiography Images", Acad Radiol 2005 12:782.

J. Liang, et al., "A Fast Toboggan-based Method for Automatic Detection and Segmentation of Pulmonary Embolism in CT Angiography", MICCAI 2005 Short Papers.

E. Pichon, et al., "A novel method for pulmonary emboli visualization from high-resolution CT images", Medical Imaging 2004: Proc. SPIE vol. 5367.

A.P. Kiraly, et al., "Analysis of aterial sub-trees affected by Pulmonary Emboli", Medical Imaging 2004: Image Processing, Proc. SPIE vol. 5370.

* cited by examiner

*Primary Examiner* — Abolfazl Tabatabai
(74) *Attorney, Agent, or Firm* — Global Patent Operation; Jonathan E. Thomas

(57) ABSTRACT

A method of identifying one or more occlusions in vasculature located in a region of interest, includes extracting vasculature from the region of interest; identifying a subject geometry of the extracted vasculature; and comparing the subject geometry to a predetermined geometry to identify a blockage. A device for identifying one or more occlusions in vasculature located in a region of interest is also presented.

18 Claims, 4 Drawing Sheets

DEVICE AND METHOD FOR IDENTIFYING OCCLUSIONS

BACKGROUND OF THE INVENTION

1. Field of the Invention

The subject matter described herein relates generally to imaging and, more particularly, to imaging occlusions in vascular tissue.

2. Related Art

Diagnostic systems provide, e.g., in the field of medicine, medical personnel with information necessary to better diagnose a medical condition. For example where a patient is complaining of severe chest pain, an occlusion or a blockage such as a pulmonary embolism (PE) is one of number of possible causes that must be ruled out. In the past, the occurrence of PE was diagnosed through a visual assessment by a radiologist. This is both tedious and error-prone.

Accordingly, it has been proposed to use computer-aided detection (CAD) for pulmonary embolisms which, to date, has not enjoyed significant success. Most current methods today for CAD hinge primarily on the lowered local intensity of embolized regions relative to the immediate vessel vicinity.

One disadvantage to such an approach is that it is prone to concomitantly detecting vessel bifurcations, lymph nodes, pulmonary veins with low contrast, and other normal anatomy, as false positive detections. The detection task is further hindered because of considerable variation in absolute contrast-levels, and the distribution of contrast, between different cases. In addition, contrast-pooling effects and other imaging artifacts such as motion, that alter intensity, further complicate the analysis.

One attempt to overcome false positive detection is described in the publication Y. Masutani, H. MacMahon, K. Doi, "Computerized Detection of Pulmonary Embolism in Spiral CT Angiography Based on Volumetric Image Analysis", IEEE Transactions On Medical Imaging 2002, 21(12), 1517). This publication describes detecting PE using local intensity contrast to identify groups of voxels within vasculature that are less opacified relative to their neighbors along with using curvilinearity properties of voxels to detect PE. A classifier developed using a training database of cases is employed to overcome false positive detection. Disadvantages to this approach include that it requires significant time to develop the training database and that it is very fragile if the acquisition parameters change between the training data set and clinical practice.

Liang et al (J. Liang, M. Wolf and M. Salganicoff, "A Fast Toboggan-based Method for Automatic Detection and Segmentation of Pulmonary Embolism in CT Angiography", MICCAI 2005 Short Papers) describe detecting emboli in the range of −50 HU to 100 HU using a Toboggan algorithm that clusters voxels locally, by mapping every voxel to the lowest intensity voxel in proximity to it. One disadvantage to this approach is that since contrast CT cases are prone to variations in intensity, assumptions about the intensity ranges for emboli are likely to be inadequate in cases of exceptionally severe emboli, or in cases where partial volume effects produce artificially elevated intensity levels.

Zhou et al (C. Zhou et al., "Preliminary Investigation of Computer-aided Detection of Pulmonary Embolism in Three dimensional Computed Tomography Pulmonary Angiography Images", Acad Radiol 2005; 12:782) employ a three-tiered Expectation Maximization algorithm to develop a semi-automated method for segmenting PE.

Also, attempts have been made to develop automated methods for PE visualization. For example, E. Pichon, C. L. Novak, A. P. Kiraly, "System and method for visualization of PE from high resolution CT images", US Patent Application Pub. No. US2005/0240094 A1 and E. Pichon, C. L. Novak, A. P. Kiraly, D. Naidich, "A novel method for pulmonary emboli visualization from high-resolution CT images", Medical Imaging 2004: Proc. SPIE Vol. 5367 each describe a maximum-descent technique to compute the statistics of vessel voxels radially to a centerline. In this way, a suitable statistic (minimum/average) of this set is assigned to all the voxels along the path to the centerline, bringing interiorly located PEs to the vessel surface. In another example, A. P. Kiraly, C. L. Novak, "System and Method for Tree Projection for Detection of Pulmonary Embolism", U.S. Patent Application Publication No. US2006/0025674 A1, describes a variant of Pichon et al's method which uses a cart-wheel projection in lieu of a maximum-descent. In another example, A. P. Kiraly, C. L. Novak, "System and Method for Tree-Model Visualization for Pulmonary Embolism Detection", U.S. Patent Application Publication No. US2006/0023925 A1 describes a minimum-intensity projection method that was used and the resultant vessel surface was unrolled to create a two dimensional representation of the vessel, which was used to highlight PE locations in a two dimensional delineation of the complete vessel tree. In a further example, A. P. Kiraly, E. Pichon, D. Naidich, C. L. Novak, "Analysis of arterial sub-trees affected by Pulmonary Emboli", Medical Imaging 2004: Image Processing, Proc. SPIE Vol. 5370 describes a method whereby, given a location of an embolism, the affected lung area may be identified by extracting an arterial tree distal to the PE location.

However, to date, no suitable device or method of detecting occlusions is available which overcomes the problems and disadvantages described above.

BRIEF DESCRIPTION OF THE INVENTION

In accordance with an embodiment of the present invention, a method of identifying one or more occlusions in vasculature located in a region of interest, comprises extracting vasculature from the region of interest; identifying a subject geometry of the extracted vasculature; and comparing the subject geometry to a predetermined geometry to identify a blockage.

In accordance with another embodiment of the present invention a device for identifying one or more occlusions in vasculature located in a region of interest, comprises a scanning device for generating volumetric image data and a processor configured to extract vasculature from the image data, identify a subject geometry of the extracted vasculature and compare the subject geometry to a predetermined geometry to identify a blockage.

BRIEF DESCRIPTION OF THE DRAWINGS

The following detailed description is made with reference to the accompanying drawings, in which.

DETAILED DESCRIPTION OF THE PREFERRED EMBODIMENT

One embodiment of the present invention concerns a method and a device for detecting blockages or occlusions such as pulmonary emboli in vasculature. As described in more detail below, a geometrical analysis of local shape properties of a vasculature, that may be extracted based on an intensity threshold, is employed. It can be seen that analysis of the local shape properties is invariant to intensity scaling and therefore provides a criterion that is robust to inter-case intensity variations thereby overcoming this and other disadvantages of the prior art described above.

Figure 1:
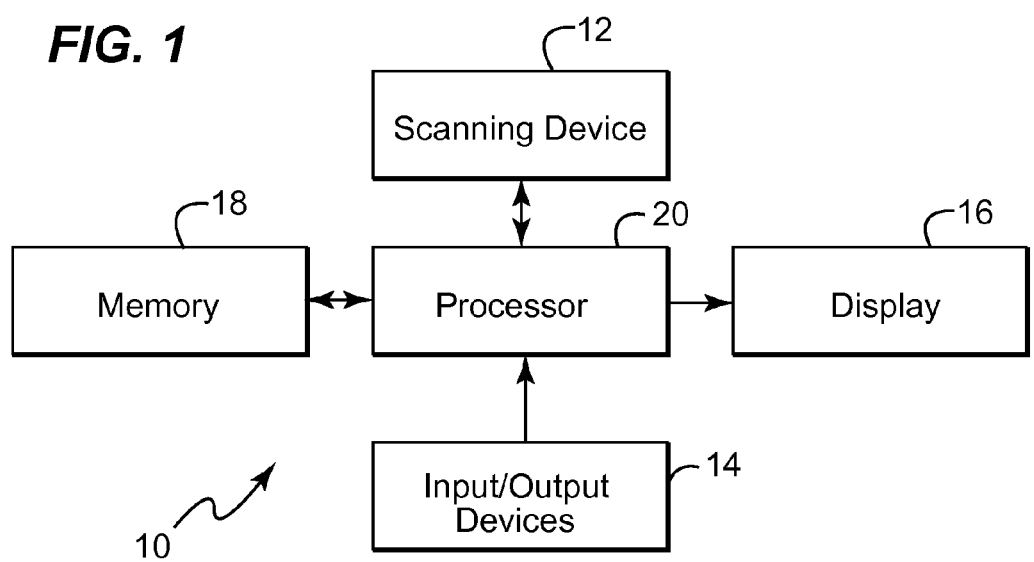
FIG. 1 is a schematic diagram showing an apparatus for identifying occlusions in accordance with one embodiment of the present invention.

Referring now to FIG. 1, an imaging device for identifying occlusions in accordance with one embodiment of the present invention is illustrated generally at 10. In this embodiment, the imaging device 10 comprises a scanning device 12, input/output devices 14, a display 16, memory 18 and a processor 20.

The scanning device 12 may be one or more devices such as a magnetic resonance (MR) imaging device, a computed tomography (CT) imaging device, a helical CT device, a positron emission tomography (PET) device, a two dimensional (2D) or three-dimensional (3D) fluoroscopic imaging device, a 2D, 3D, or four dimensional ultrasound imaging device, and/or an x-ray device, that is capable of generating volumetric image data and communicating this data to the processor 20.

The input/output devices 14 may comprise any number or combination of devices capable of providing information to and/or received from the processor 20 such as a keyboard, a CD/DVD drive, flash memory and/or a printer. The display 16 may comprise any suitable display monitor such as a liquid crystal display.

The memory 18 may comprise any suitable short term memory, such as RAM and/or ROM, and/or long term memory, such as a hard disk, for storing information used by the processor 20 to carry out any of the below described functions and any others required by the practice of this invention.

The processor 20 may be any suitable device that is capable of being configured by a series of instructions provided, for example, in firmware or software and, as shown, is connected in circuit to communicate with each of the scanning device 12, input/output devices 14, display 16 and memory 18. In one embodiment of the present invention, the processor 20 is configured to detect an occlusion or blockage such as a pulmonary embolism. To achieve this, and in the event that pulmonary emboli for which the flow of contrast is sufficient such that the vasculature or vessel segments can be easily traced past the point of the blockage, the processor 20 may be configured to detect dark pathology within a bright field representing vasculature. As described in detail below, where it is the case that severe pulmonary emboli render incomplete one or more affected vessel segments in a vascular tree, vasculature may be additionally extracted as a series of bifurcations and segments, in a graph-representation. This may then be compared with a baseline or a standard atlas of lung vessels in order to pinpoint breaks in the anatomy.

In this exemplary embodiment, volumetric image data of a pair of lungs may be produced by the scanning device 12 and communicated to the processor 20 which may be configured to first provide smoothing of the image data to reduce the effect of noise. Thereafter, lungs may be extracted from the image data by setting an intensity threshold. It will be appreciated that the remaining image data will, in general, not contain vessels or structures on the lung wall. To correct for this, a morphological closing may be applied to include the wall structures, followed by a known hole-filling step to include the parenchymal structures.

Thereafter, a vascular tree may be extracted from the now contrast enhanced CT volumetric image data using a shape-based or geometrical analysis. In this way, pulmonary vessels may be segmented by analyzing a local curvature response of voxels within the image data containing the lung fields. In accordance with an important feature of this embodiment, it will be appreciated that at any given location, a ratio of eigenvalues k1, k2 of a curvature tensor provides information about a local shape of an isosurface intersecting the given location, with values close to zero and to one for curvilinear (vessel) and spherical (globular) objects respectively.

More specifically, principal curvatures of an isosurface I(x)=k at a location x may be found from the eigenvalues of a 2×2 matrix C, referred to as the curvature tensor of volumetric image data, I:

$$C = -\frac{N^t H N}{\|\nabla I\|}$$

where H is the 3×3 Hessian matrix of second derivatives of the volume image data, and N is the 3×2 matrix of the null space of ∇I.

At any given location, the eigenvalues $\kappa_{1,2}$ of the curvature tensor provide information about the local shape of the isosurface intersecting that location. The analysis of tensor curvatures provides local geometric properties that are invariant under, and robust to, the intensity scaling associated with the prior art.

It is has been found that a curvilinear structure such as a vessel displays a marked difference in the magnitudes of $\kappa_1$ and $\kappa_2$, whereas, in contrast, spherical structures are characterized by nearly equal values of $\kappa_1$ and $\kappa_2$. Therefore, a ratio of extracted curvature tensors at a voxel provides an important identifying feature for a vessel.

Also, by imposing a minimum threshold on the curvature tensor, e.g., $(1-\kappa_1/\kappa_2)$, in addition to an intensity threshold, described below, vessel voxels may be segmented within the volumetric image data of the lung fields to better reveal pulmonary emboli.

Figure 2:
FIG. 2 is a section of a contrast image of a lung showing segmented vessels.

It will be appreciated that pulmonary emboli appear as dark cylinders/dark spheres within a bright vessel field and, because of this, the derived tensor curvatures calculated include a reverse sign for these structures. This may be used to detect deviations from the normal curvature responses for bright vessels. FIG. 2 illustrates a section of a contrast CT image showing the complexity of pulmonary vessels and pulmonary emboli. It will be understood that a method and device in accordance with one embodiment of the present invention, as described in more detail below, are able to find PE's within these pulmonary vessels and detect discontinuities in the imaging of the contrast enhanced vessels.

Figure 3:
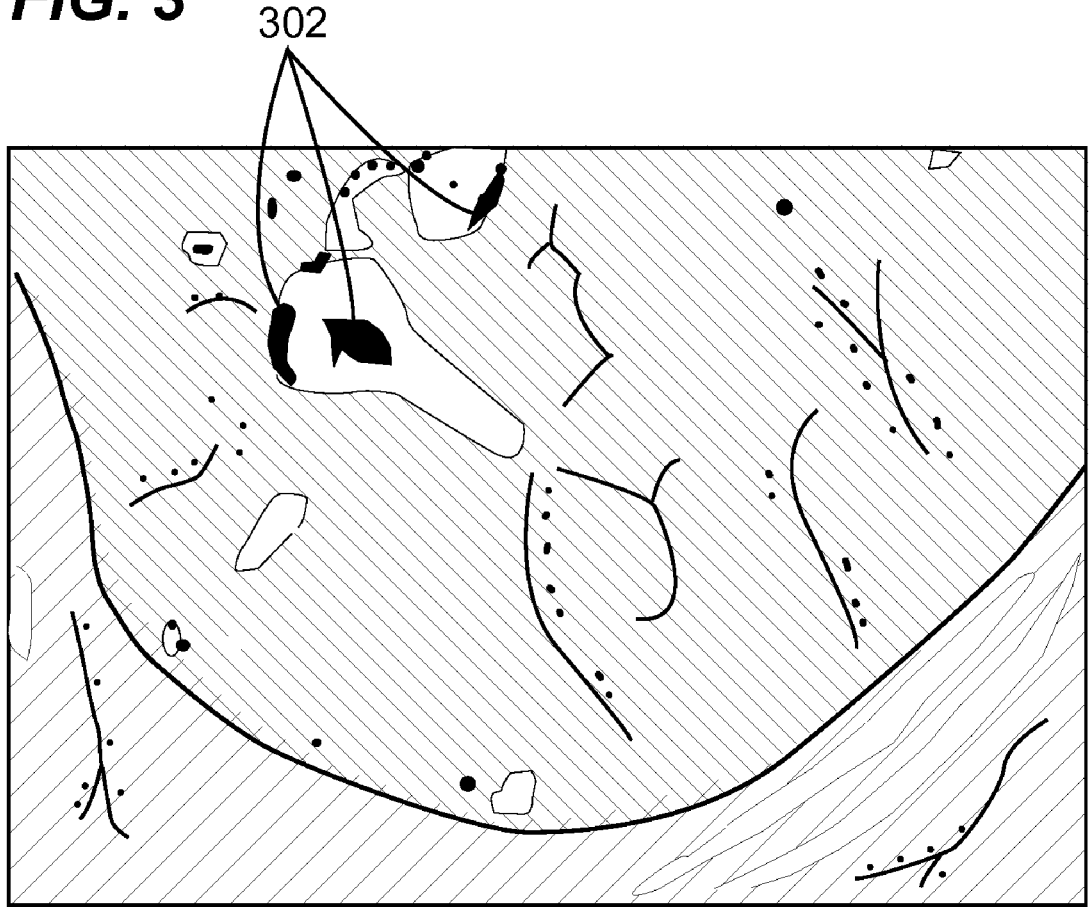
FIG. 3 is another section of a contrast image of a lung showing curvature of a vessel including an occlusion.

FIG. 3 shows another section of a contrast CT image where an occlusion central to a vessel is highlighted at 302 in a curvature response map. This section shows the occlusion located within a generally spherical structure.

For blockages that more severely impede the flow such that the tree is either discontinuous or terminates at the point of blockage, it will be important to recognize sufficient portions of an anatomy such that discontinuities and terminations can be reconciled with the normal limits of the ability to detect vasculature. This may supplement the above-described geometrical analysis in situations where the emboli prevent such geometric analysis of the very vessel segment that is affected. For example, locations where the pulmonary tree under consideration is either discontinuous (after subjecting the volumetric image data to an intensity threshold) or where a subject graph differs from the control graph by indicating breaks in the pulmonary flow, that can be considered indicative of possible pulmonary embolism.

To prepare a subject graph representation of an anatomy under consideration, image data representing vasculature may be identified through bifurcation points and vasculature segments. The subject graph can then be compared against a predetermined graph or reference anatomy that is a representation of a structure of the lung (or other organ) vasculature without emboli. The predetermined graph can be a baseline or a different scan of the same individual either with or without contrast from which a "full" vasculature tree may be extracted with a level of confidence, or, since the vasculature tree generally has a fixed topology for large portions of the population, it can be an anatomical atlas. The geometrical analysis, described above, is used to build up a vascular tree from the segments and junctures of the scan under consideration and this tree is then labeled in a fashion to preserve the underlying topology. It can be seen that discontinuities in the graph and places where the graph topology differs from the topology of the reference anatomy can be considered candidate PE locations.

In accordance with another embodiment of the present invention, a method of identifying one or more occlusions in vasculature located in a region of interest, is shown generally at 400 and as shown at 402, comprises extracting vasculature from the region of interest. As shown at 404, the method also comprises identifying a subject geometry of the extracted vasculature and, as shown at 406, comparing the subject geometry to a predetermined geometry to identify a blockage. The method may further comprise, as shown at 408, generating a subject graph representative of the vasculature extracted, providing a predetermined graph, as shown at 410, and comparing the subject graph with the predetermined graph to detect missing or abnormal graph segments and thereby identify a blockage, as shown at 412.

Also in accordance with the method 400, the step of identifying a subject geometry may comprise using a curvature tensor to identify a shape of an isosurface of the extracted vasculature, as shown at 414. It will be understood that the curvature tensor may comprise a ratio of Eigenvectors that correspond to the shape of the isosurface as shown at 416.

Further in accordance with the method 400, the step of extracting vasculature may comprise using computed tomography to generate volumetric image data and generating lung vasculature from the volumetric image data. Also, the step of extracting vasculature may further comprise setting an intensity threshold for the volumetric image data to separate lung vasculature as shown at 418. Further, the step of extracting vasculature may still further comprise applying a morphological closing to the volumetric image data to generate lung wall structures and providing a hole filling scheme to replicate parenchymal structures. It will be understood that the blockage may be a pulmonary embolism and that the predetermined graph may comprise a baseline graph or an anatomical atlas.

The present invention adopts an approach to better understand the characteristics of an embolus structure itself, thereby reducing false detections at the very start. Also, the analysis extends beyond the local response by identifying an embolus as an element of the global pulmonary vessel tree that deviates from an atlas beyond an allowable degree. This permits the identification of complete occlusions that would ordinarily be missed by geometric analysis, and thereby excluded from the field of search. Identification of emboli with reference to their anatomic location in a model tree would also help reduce the misidentification of pulmonary veins that have inconsistent opacification as erroneous emboli sites.

Technical effects of the herein described systems and methods include identifying a subject geometry of an extracted vasculature and comparing the subject geometry to a predetermined geometry to identify a blockage.

While the present invention has been described in connection with what are presently considered to be the most practical and preferred embodiments, it is to be understood that the present invention is not limited to these herein disclosed embodiments. Rather, the present invention is intended to cover all of the various modifications and equivalent arrangements included within the spirit and scope of the appended claims.

What is claimed is:

1. A method of identifying one or more occlusions in vasculature located in a region of interest of image data, comprising:
    extracting vasculature from the region of interest of image data;
    identifying a subject geometry of the extracted vasculature;
    generating a subject graph representative of the vasculature extracted;
    accessing a predetermined graph; and
    comparing both the subject graph with the predetermined graph to detect missing or abnormal graph segments and the subject geometry to a predetermined geometry and thereby identify a blockage.

2. The method of claim 1, wherein identifying a subject geometry comprises using a curvature tensor to identify a shape of an isosurface of the extracted vasculature.

3. The method of claim 2, wherein the curvature tensor comprises a ratio of Eigenvectors that correspond to the shape of the isosurface.

4. The method of claim 1, wherein extracting vasculature comprises using computed tomography to generate volumetric image data and determining lung vasculature from the volumetric image data.

5. The method of claim 4, wherein extracting vasculature further comprises setting an intensity threshold for the volumetric image data to separate lung vasculature.

6. The method of claim 5, wherein extracting vasculature further comprises:
    applying a morphological closing to the volumetric image data to generate lung wall structures; and
    providing a hole filling scheme to replicate parenchymal structures.

7. The method of claim 1, wherein the blockage is a pulmonary embolism.

8. The method of claim 1, wherein the predetermined graph comprises a baseline graph.

9. The method of claim 1, wherein the predetermined graph comprises an anatomical atlas.

10. A device for identifying one or more occlusions in vasculature located in a region of interest of image data, comprising:
    a scanning device for generating volumetric image data;
    a processor configured to extract vasculature from the image data, identify a subject geometry of the extracted vasculature; generate a subject graph representative of the vasculature extracted; and compare both the subject graph with a predetermined graph to detect missing or abnormal graph segments and compare the subject geometry of to a predefined geometry and thereby identify a blockage.

11. The device of claim 10, wherein the processor employs a curvature tensor to identify a shape of an isosurface of the extracted vasculature.

12. The device of claim 11, wherein the curvature tensor comprises a ratio of Eigenvectors that correspond to the shape of the isosurface.

13. The device of claim 10, wherein the scanning device uses computed tomography to generate the volumetric image data and wherein the vasculature comprises lung vasculature.

14. The device of claim 13, wherein the processor is further configured to set an intensity threshold for the volumetric image data to separate lung vasculature.

15. The device of claim 14, wherein the processor is further configured to:
    apply a morphological closing to the volumetric image data to generate lung wall structures; and
    provide a hole filling scheme to replicate parenchymal structures.

16. The device of claim 10, wherein the blockage is a pulmonary embolism.

17. The method of claim 10, wherein the predetermined graph comprises a baseline graph.

18. The method of claim 10, wherein the predetermined graph comprises an anatomical atlas.

* * * * *

UNITED STATES PATENT AND TRADEMARK OFFICE
CERTIFICATE OF CORRECTION

PATENT NO. : 7,965,810 B2  
APPLICATION NO. : 11/768623  
DATED : June 21, 2011  
INVENTOR(S) : Roy et al.

Page 1 of 1

It is certified that error appears in the above-identified patent and that said Letters Patent is hereby corrected as shown below:

On the Title Page, item (75), under "Inventors", in Column 1, Line 1, delete "Banglore" and insert -- Bangalore --, therefor.

On the Title Page, item (56), under "OTHER PUBLICATIONS", in Column 2, Line 15, delete "aterial" and insert -- arterial --, therefor.

Figure 4:
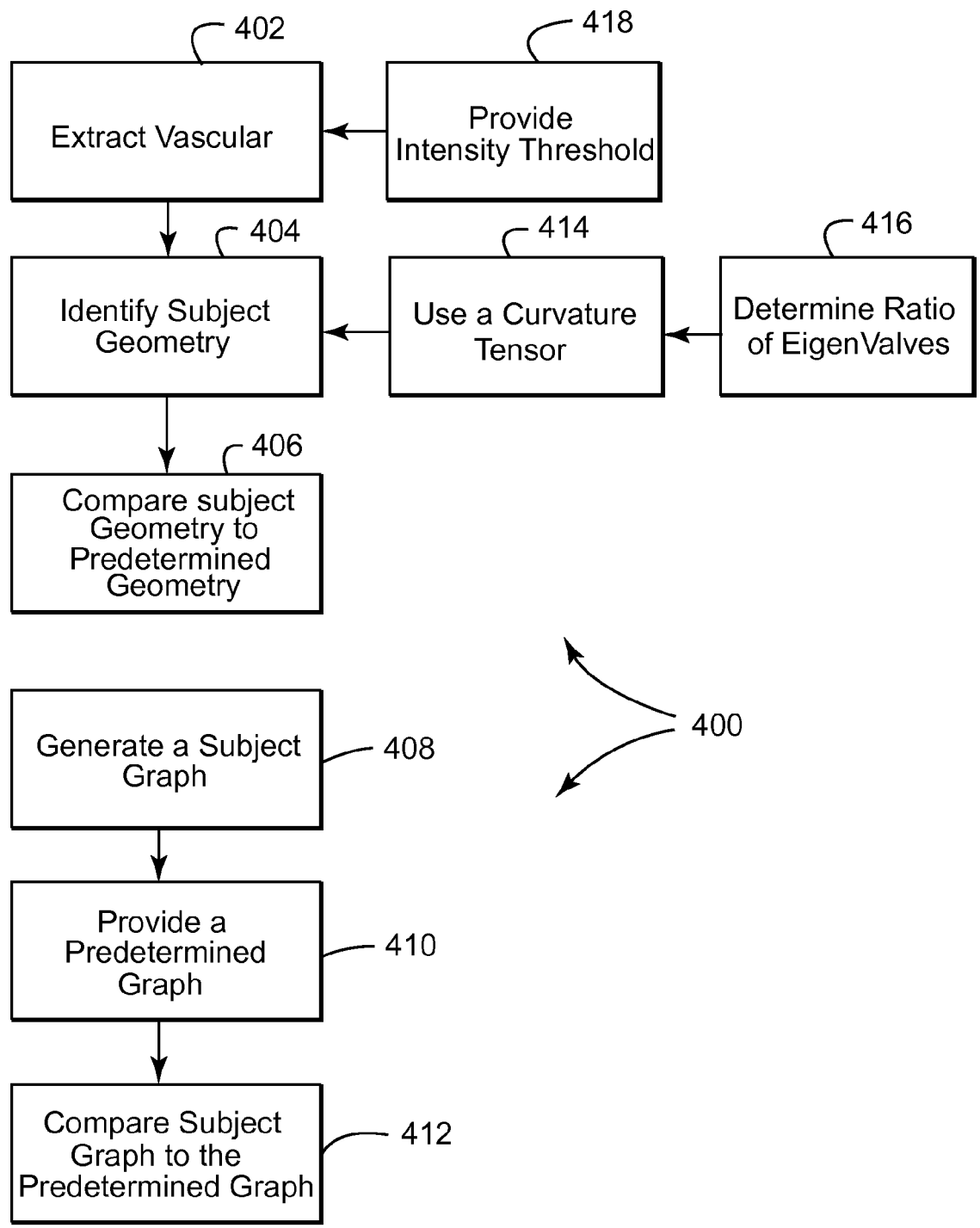
FIG. 4 is a flow diagram illustrating a method for identifying occlusions in accordance with another embodiment of the present invention.

In Fig. 4, Sheet 4 of 4, For Tag "416", in Line 2, delete "Eigen Valves" and insert -- EigenValues --, therefor.

In Column 7, Line 2, in Claim 10, delete "of to a predefined" and insert -- to a predefined --, therefor.

In Column 8, Line 9, in Claim 17, delete "method" and insert -- device --, therefor.

In Column 8, Line 11, in Claim 18, delete "method" and insert -- device --, therefor.

Signed and Sealed this  
Eighteenth Day of October, 2011

David J. Kappos  
*Director of the United States Patent and Trademark Office*